(12) United States Patent
Pierson et al.

(10) Patent No.: US 8,293,120 B2
(45) Date of Patent: Oct. 23, 2012

(54) WET CYCLONE PARTICLE COLLECTOR

(75) Inventors: Raymond M. Pierson, Millersville, MD (US); Matthew P. Szarek, Dundalk, MD (US); Thomas G. Stroka, Crofton, MD (US); Andrew R. McFarland, Houston, TX (US)

(73) Assignees: Northrop Grumman Systems Corporation, Falls Church, VA (US); The Texas A&M University System, College Station, TX (US)

( * ) Notice: Subject to any disclaimer, the term of this patent is extended or adjusted under 35 U.S.C. 154(b) by 585 days.

(21) Appl. No.: 12/461,447

(22) Filed: Aug. 12, 2009

(65) Prior Publication Data

US 2011/0039679 A1 Feb. 17, 2011

(51) Int. Cl.
*B01D 45/10* (2006.01)
*B04B 11/04* (2006.01)
*B04B 11/06* (2006.01)
*B04B 15/02* (2006.01)

(52) U.S. Cl. ............. 210/788; 210/512.1; 209/722; 209/725; 96/316; 96/321; 96/413; 95/219; 95/220; 73/863.11; 73/863.12; 55/392.1; 55/459.1

(58) Field of Classification Search ............. 210/512.1, 210/788; 209/722, 725; 96/316, 321, 413; 95/219, 220; 73/863.11, 863.12; 55/392.1, 55/459.1
See application file for complete search history.

(56) References Cited

U.S. PATENT DOCUMENTS

2009/0193971 A1* 8/2009 McFarland et al. ............ 95/220
* cited by examiner

*Primary Examiner* — David A Reifsnyder
(74) *Attorney, Agent, or Firm* — Andrews Kurth LLP

(57) ABSTRACT

A wet cyclone particle collector is disclosed. The wet cyclone particle collector includes a cyclone unit, a liquid delivery unit and a sample collection unit. The cyclone unit draws a gas sample into a cyclone chamber and creates a circular flow of the gas sample inside the cyclone chamber so that particles in the gas sample are separated from said gas sample by centrifugation force. The liquid delivery unit delivers a collection liquid into the cyclone in a non-continuous fashion. The sample collection unit harvests the collection liquid from the cyclone unit. The non-continuous delivery of the collection liquid significantly reduces consumption of collection liquid during operation of the particle collector.

20 Claims, 4 Drawing Sheets

WET CYCLONE PARTICLE COLLECTOR

FIELD OF INVENTION

This invention relates to a particle collector and in particular to a wet cyclone particle collector with reduced liquid consumption.

BACKGROUND

Cyclone particle collectors are mechanical devices used for the collection of particles and/or aerosols. Briefly, the collector creates a "cyclonic" or centrifugal force to separate particles/aerosols from an air sample stream. The centrifugal force is created when the air sample enters the top of the collector at an angle and is spun rapidly downward in a vortex (similar to a whirlpool action). As the air sample flow moves in a circular fashion downward, heavier particles are thrown against the walls of the collector and slide down into a hopper to be collected. In a wet cyclone collector, the collector walls are covered with a layer of liquid, which traps the particles as they hit the wall and improves collection efficiency. A major disadvantage for wet cyclone collectors, however, is that they typically consume large amounts of collection fluid during the operation period. The quantity of consumables is prohibitory to many kinds of applications, especially those applications that require continuous collection for an extended period of time at a location that is not easily accessible.

Therefore, there is a need for a wet cyclone particle collector with minimal liquid consumption.

SUMMARY OF THE INVENTION

A particle collector is disclosed. The particle collector includes a cyclone unit, a liquid delivery unit and a sample collection unit. The cyclone unit draws in a gas sample and creates a circular flow of the gas sample so that particles in the gas sample are separated from the gas sample by centrifugation force. The liquid delivery unit delivers a collection liquid in a non-continuous fashion into the cyclone unit. The liquid delivery unit includes a collection liquid tank, a pump that maintains a positive pressure in the collection liquid tank, and a valve that controls delivery of the collection liquid to the cyclone unit. The sample collection unit harvests the collection liquid from the cyclone unit.

Also disclosed is a method for collecting particles from a gas sample. The method includes introducing the gas sample into a cyclone chamber in a circular flow so that particles in the gas sample are separated from the gas sample by centrifugation force, introducing a collection liquid in a non-continuous fashion into the cyclone chamber so that the collection liquid forms a thin liquid layer on an inner wall of the cyclone chamber and traps particles impacting on the inner wall, and harvesting the collection liquid from the cyclone chamber. The collection liquid is introduced into the cyclone chamber from a collection liquid tank maintained under a positive pressure via a valve with a duty cycle of 5% to 50%.

BRIEF DESCRIPTION OF DRAWINGS

In the accompanying drawings, forming part of the specification, like numerals are employed to designate like parts throughout the same.

DETAILED DESCRIPTION

In describing various embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

Figure 1:
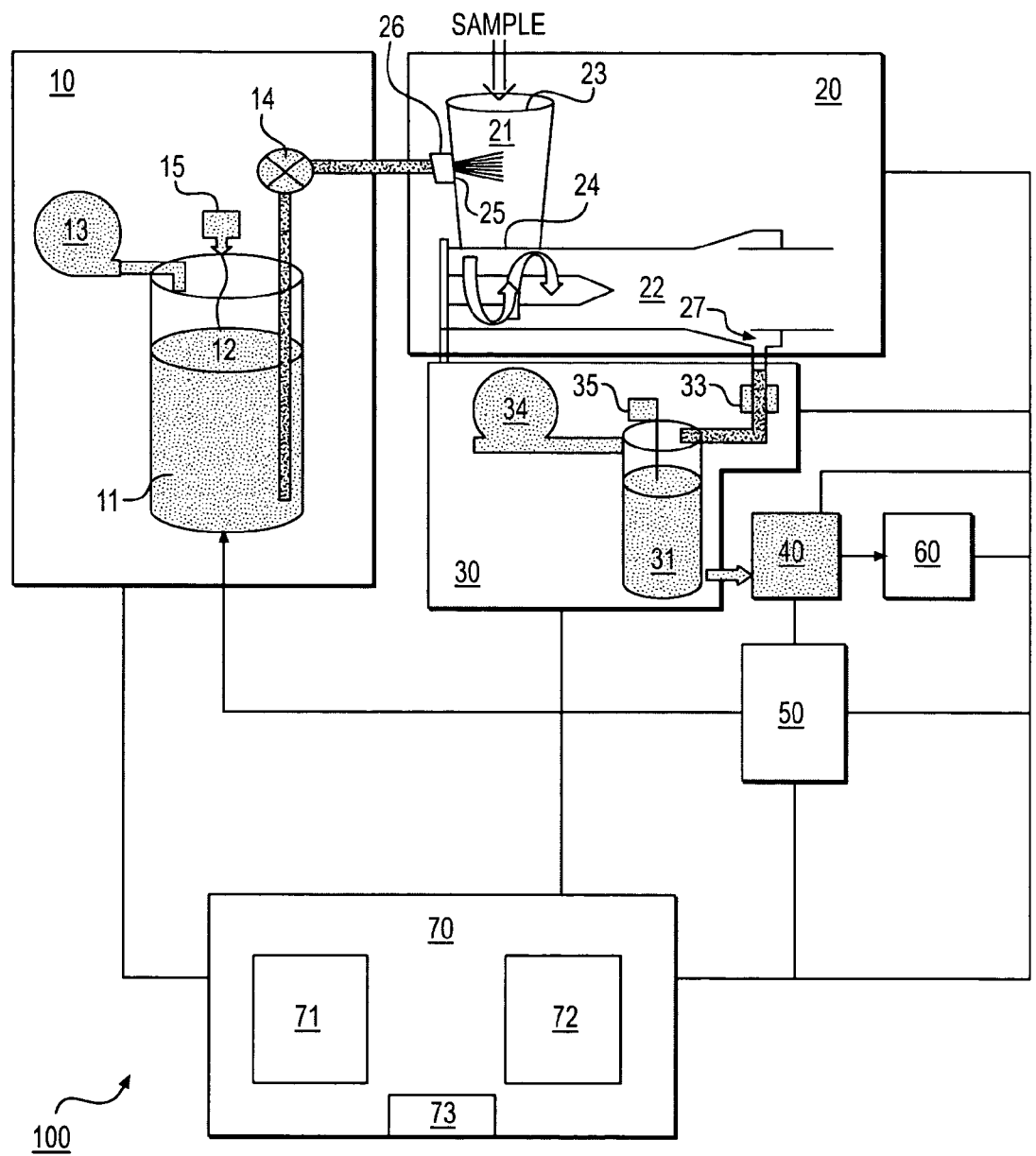
FIG. 1 is a block diagram showing an embodiment of a wet cyclone particle collector.

A wet cyclone particle collector is disclosed. Referring now to FIG. 1, an embodiment of the wet cyclone particle collector 100 includes a collection liquid delivery unit 10, a cyclone unit 20, and a sample collection unit 30. The cyclone unit 20 draws in a gas sample and creates a circular flow of the gas sample so that particles in the gas sample are spun against a cyclone wall by centrifugation force. The collection liquid delivery unit 10 delivers a collection liquid in a non-continuous fashion into the cyclone unit 20. The collection liquid passes through the cyclone unit 20 along the cyclone wall, collects particles impacting on the cyclone wall during the passage, and enters the particle sample collection unit 30 at a collection point of the cyclone unit to be recycled, stored, or transferred for further analysis.

The term "gas sample," as used herein, refers to any gaseous samples including air samples.

The term "particle," as used herein, refers to both the solid particles and liquid droplets. The particles can be aerosols of a biowarfare agent (e.g., bacteria, viruses, etc.) or other microorganisms, a chemical warfare agent, a toxic industrial chemical.

The phrase "delivers in a non-continuous fashion," as used herein, refers to an intermittent delivery of the collection liquid to a continuous flow of the gas sample. In other words, while the cyclone unit 20 draws in the gas sample as a continuous sample flow, the collection liquid delivery unit 10 delivers the collection liquid in a pulse-like manner. e.g., by one-second long injections with an interval of nine seconds between injections.

In the embodiment shown in FIG. 1, the collection liquid delivery unit 10 includes a collection liquid tank 11, collection liquid 12, a pump 13, and valve 14. The collection liquid 12 is a liquid with a low evaporation rate and a neutral pH. The low evaporation rate reduces the consumption rate of the collection liquid 12, and the neutral pH preserves the viability of the collected microorganism. Examples of the collection liquid include, but are not limited to, water, saline, phosphate buffered saline, ethylene glycol solutions and polyethylene glycol (PEG) solutions.

In one embodiment, the collection liquid further contains a surfactant. Examples of surfactants include, but are not limited to, nonionic surfactants such as polysorbates (e.g., Tween 20, Tween 80 and dodecyl dimethylamine oxide), alkyl polyethylene oxide, alkylphenol polyethylene oxide, poloxamers, poloxamines, alkyl polyglucosides (e.g., octyl glucoside and decyl maltoside, fatty alcohols (e.g., cetyl alcohol and oleyl alcohol), cocamide MEA and cocamide DEA; anionic surfactants such as perfluorooctanoate (PFOA or PFO), perfluorooctanesulfonate (PFOS), sodium dodecyl sulfate (SDS), ammonium lauryl sulfate, sodium laureth sulfate, alkyl benzene sulfonate, soaps, and fatty acid salts; cationic surfactants such as cetyl trimethylammonium bromide (CTAB) and other alkyltrimethylammonium salts, cetylpyridinium chloride (CPC), polyethoxylated tallow amine (POEA), benzalkonium chloride (BAC), and benzethonium chloride (BZT); and zwitterionic surfactants such as dodecyl betaine, cocamidopropyl betaine and coco ampho glycinate. The surfactants may be used in a concentration range of 0.005% to 0.5% by volume, and more preferably 0.01% to 0.1% by volume.

The pump 13 is used to maintain a positive pressure in the collection liquid tank 11. The pressure of the collection liquid tank 11 may be monitored by a pressure sensor 16. In one embodiment, the pump 13 is a diaphragm pump. The valve 14 controls the flow of the collection liquid 12 into the cyclone unit 20. In one embodiment, the collection liquid delivery unit 10 further includes a pressure sensor 15 that monitors the pressure in the collection liquid tank 11.

Figure 2B:
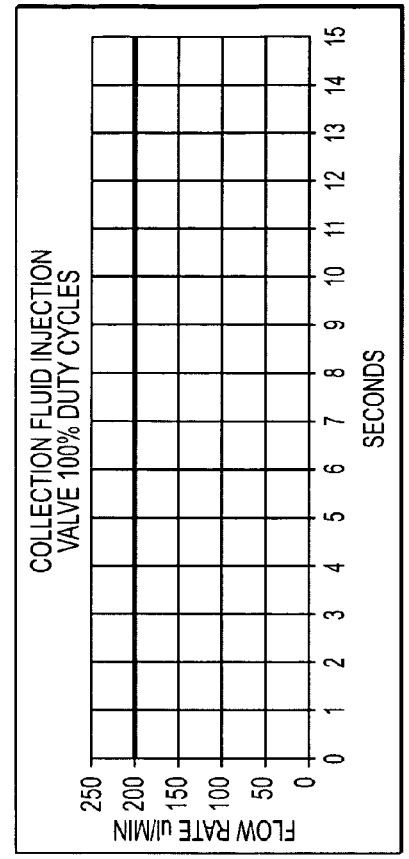
FIGS. 2A and 2B are diagrams showing collection liquid flow rate at different duty cycles.
Figure 2B:
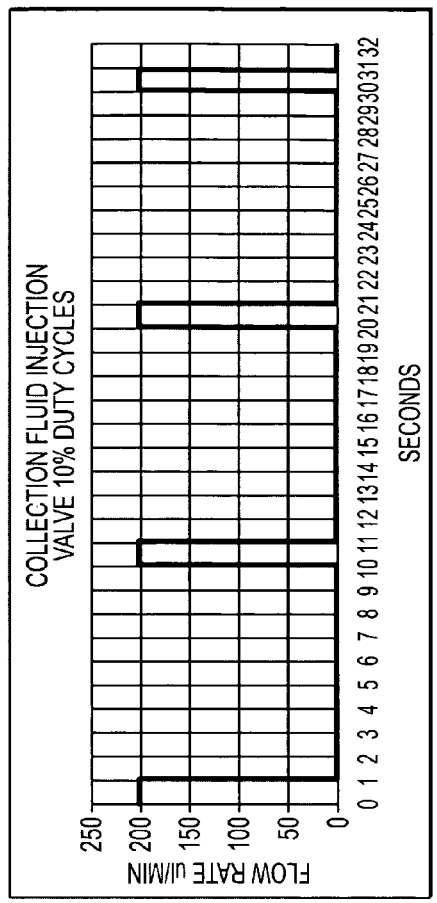
Figure 2B:
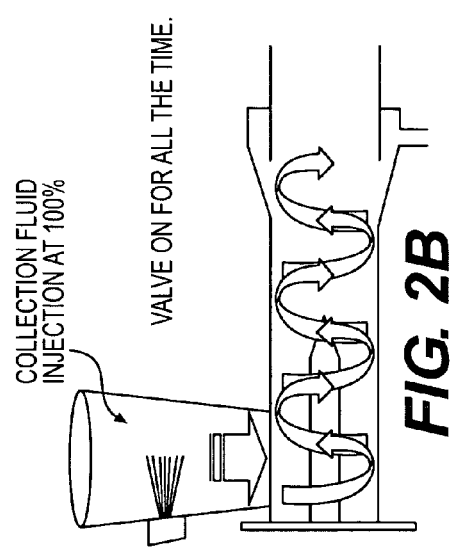
Figure 2A:
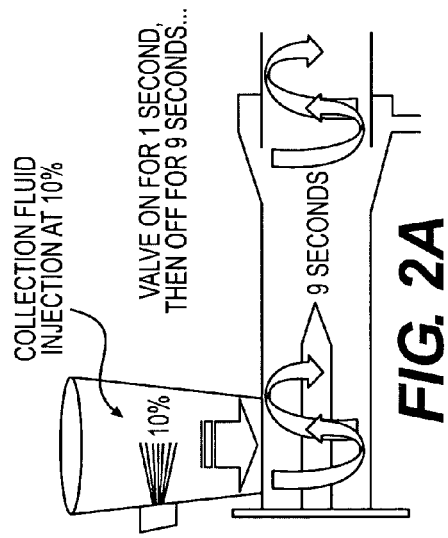

Depending on the specific need of a particular application, the valve 14 may operate on a duty cycle of 5%, 10%, 20%, 30%, 40% and 50%. As used hereinafter, a 10% duty cycle refers to a status that the valve remains open 10% of the time during a cycle. For example, a 10% duty cycle with a cycling time of 10 seconds means that valve opens for one second and closes for 9 seconds during each cycle. A 100% duty cycle refers to a status that the valve stays open all the time during a cycle. In certain embodiments, the valve 14 is a solenoid valve with electronically controlled duty cycles. FIG. 2 shows an exemplary flow rate of the collection liquid 12 with the solenoid valve 14 operating at the 10% duty cycle (FIG. 2A) and 100% duty cycle (FIG. 2B). Alternatively, the collection liquid 12 may be injected into the aerosolization chamber 21 in a non-continuous manner (e.g., periodic injection every five seconds) using other injection devices known to one skilled in the art, such as a syringe injector.

The cyclone unit 20 includes an aerosolization chamber 21 and a cyclone chamber 22. The gas sample enters the aerosolization chamber 21 from the gas sample inlet 23 and then enters the cyclone chamber 22 through sample inlet 24. In one embodiment, the aerosolization chamber 21 is tangentially coupled to the side of cyclone chamber 22 such as the gas sample flows in to the cyclone chamber 22 in a direction generally tangent to the circumference of inner surface of the cyclone chamber 22. This configuration facilitates the formation of a spiraling or cyclonic fluid flow inside the cyclone chamber 22.

The collection liquid 12 is injected into the aerosolization chamber 21 through collection liquid inlet 25 in a direction tangential to the gas flow. In one embodiment, collection liquid 12 enters the aerosolization chamber 21 through an air blast atomizer 26 that transforms the collection liquid into droplets. In another embodiment, the collection liquid 12 is directly injected into the cyclone 22.

Referring again to FIG. 1, after entering the aerosolization chamber 21, the droplets of the collection liquid 12 are entrained by the gas flow entering the cyclone chamber 22. The droplets then impact on the inner wall of the cyclone chamber 22, where they form a thin liquid film onto which the particles contained in the gas flow can impact. The cyclonic motion of the gas flow inside the cyclone drives the accumulated liquid as rivulets or droplets to the sample skimmer point 27 of the cyclone chamber 22. In one embodiment, the cyclone chamber 22 has a cooled inner wall to reduce evaporation of the collection liquid 12. In another embodiment, the temperature of the inner wall is maintained at or below the dew point of the incoming gas sample to reduce evaporation of the collection liquid. In another embodiment, the inner wall temperature is maintained by a thermoelectric cooler (TEC). The TEC may also be operated in the reverse mode to provide heating to the inner wall of the cyclone chamber 22.

The particle sample collection unit 30 includes a particle sample reservoir 31 and a tubing 32 connecting the particle sample reservoir 31 to the cyclone chamber 22 at the sample skimmer point 27. A flow meter 33 measures the flow rate of the collected particle samples. A diaphragm pump 34 may be used to depressurize the particle sample reservoir 31 so that the particle-laden collection fluid collected at the sample skimmer point 27 can be gently pulled into the he particle sample reservoir 31 without having to pass through any pump that may harm fragile microorganisms. A second pressure sensor 35 may be used to monitor the pressure in the particle sample reservoir 31.

The wet cyclone particle collector 100 may further include a sample processing unit 40 that processes collected particle samples for further analysis. In one embodiment, the sample processing unit 40 includes a nucleic acid isolation device capable of extracting nucleic acids from the collected particle samples. In another embodiment, the sample processing unit 40 includes an affinity based isolation device capable of isolating an agent of interest in the collected particle samples.

The wet cyclone particle collector 100 may further include a collection liquid recycling system 50. In one embodiment, the collection liquid recycling system 50 includes a filter 51 to remove particulate matter from the waste liquid (i.e., the collection liquid collected at the skimming point) and an optional cleaning device 52 to remove soluble contaminants from the waste liquid. The collection liquid recycling system 50 may further include gravity, temperature, and pH sensors for the determination of solvate concentration and pH of the recycled collection fluid.

In one embodiment, the wet cyclone particle collector 100 further includes a detection system 60 that detects a target particle or molecule in the collected sample.

In another embodiment, the wet cyclone particle collector 100 is controlled in real time by a programmable logic controller (PLC) 70. The PLC 70 regulates the pressures in the collection liquid tank 11 and the particle sample reservoir 31, and controls the injection rate of the collection liquid 12. The flow meter 33 and pressure sensors 15, 35 provide feedback to the PLC 70, allowing the PLC 70 to adjust the injection rate to compensate for evaporation of the sample collection liquid 12. PLCs are well-known to a person of ordinary skill in the art.

In one embodiment, the PLC 70 comprises a flash memory 71 a microcontroller 72, and an external port 73. The flash memory 71 may be used to store operation software and other information. The microcontroller 72 monitors and controls the operation of the wet cyclone particle collector 100. The microcontroller 72 is preferably small, lightweight and available as a standard commercial off-the-shelf (COTS) product. In one embodiment, the microcontroller 72 is a COTS offering and is packaged as a microbox PC with a passive PCI bus backplane. This configuration allows the component modularity for easy upgrades as computer hardware technologies improve. The microcontroller 72 resides on a single board computer (SBC) that already has its peripheral interfaces built in: PCI bus, Ethernet, and RS-232 serial. Flash memory and DRAM can be sized to the control system requirements with removable memory sockets on the SBC. Communication from the microcontroller 72 to various components of the wet cyclone particle collector 100 is handled by COTS data acquisition, digital input/output, and analog input/output circuit cards that are PCI bus compatible. This approach is cost effective while meeting most commercial environmental requirements The external port 73 is used for downloading software upgrades to the flash memory 71 and performing external trouble-shooting/diagnostics. In one embodiment, the wet cyclone particle collector 100 is powered by a long-life battery or batteries that can be recharged and reused.

Figure 3:
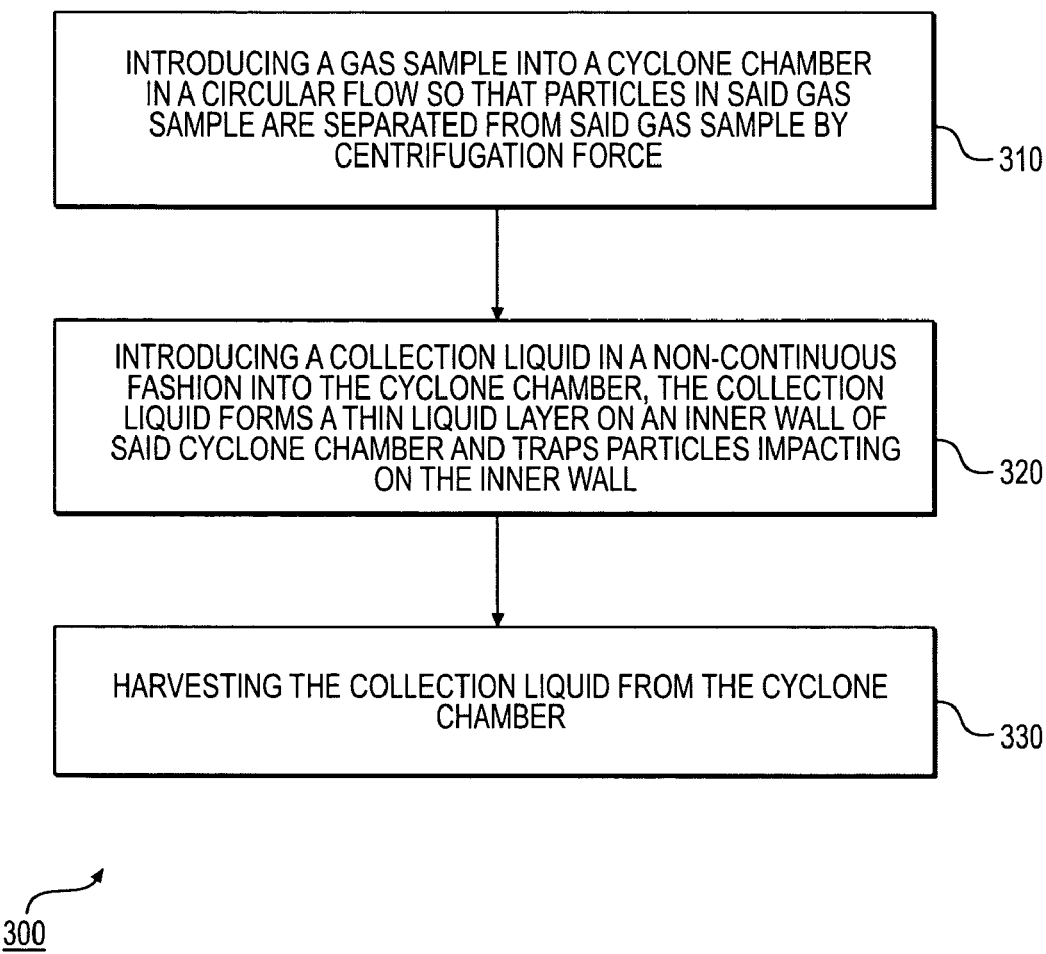
FIG. 3 is a flow diagram showing a method for collecting particles with a wet cyclone particles collector.

Also disclosed is a method for collecting particles from a gas sample. As shown in FIG. 3, an embodiment of the method 300 includes: continuously introducing (310) the gas sample into a particle collector in a circular flow, wherein centrifugal force created by the circular flow throws particles in the gas samples toward an inner wall of the particle collector by centrifugation force; periodically introducing (320) a collection liquid into the circular flow of gas sample, wherein centrifugal force created by the circular flow throws the collection liquid against the inner wall of the particle collector thus forming a thin liquid layer that traps particles in the gas sample; and harvesting (330) the collection liquid at a skimming point in the particle collector.

In one embodiment, the inner wall of said particle collector is maintained at a temperature equal to or below the dew point of the gas sample to reduce evaporation of the collection liquid.

In another embodiment, the method further includes: extracting (340) a target particle or molecule from harvested collection liquid; and recycling (350) the harvested collection liquid.

In certain embodiments, the method results in the collection of about 85% of bioaerosol particles in the size range of 1-10 μm aerodynamic diameter and a reduction of up to 80% in both liquid sample accumulation and the amount of collection liquid fed into the particle collector.

The non-continuous delivery of the collection liquid into the cyclone significantly reduces the consumption of the collection liquid, thus allowing increased field operation time and decreased operational cost. The reduction of the amount of the collection liquid also increases the concentration of particulates in the collected sample which, in turn, enhances the possibility of detection by bringing the target concentration in the collected sample above the threshold level of the detection system.

EXAMPLES

Example 1

Collection of Aerosols with Non-Continuous Liquid Flow Wet Cyclone Collector

A prototype wet cyclone device is constructed based on the concept shown in FIG. 1. The device operates by injecting a collection buffer into a cyclone in short pulses, using the diaphragm pump/solenoid valve combination shown in FIG. 1. The rate of injection is about $\frac{1}{10}^6$ that of the air flow rate. Therefore for an input air flow of 300 liters per minute the collection buffer injection rate is 300 micro liters per minute. Once injected, the liquid stream is Air Blast Atomized (ABA) as it enters the air flow; it is then deposited onto the cyclone's inner wall as rivulets, where the cyclonic motion of the air flow then drives the accumulated rivulets of the liquid to the sample skimmer. The particle rich hydrosol is collected by the skimmer and stored in a sample reservoir.

Figure 4:
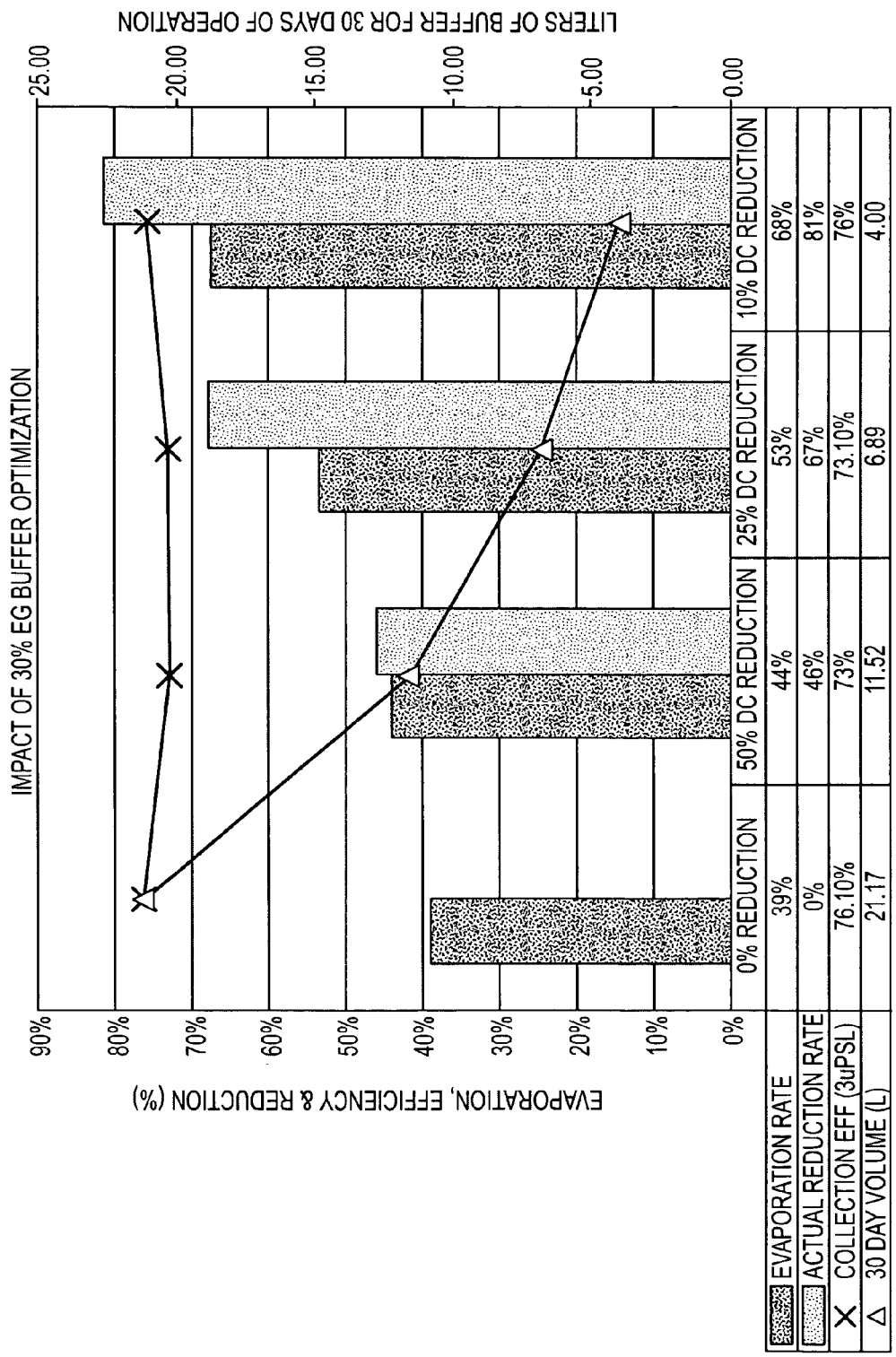
FIG. 4 is a diagram showing the impact of intermittent delivery of collection fluid on the performance of the cyclone particle collector.

As shown in FIG. 4, the pulsed operation of the collection liquid using a 10% duty cycle results in a 81% reduction in the consumption of collection liquid without impacting the cyclones general collection efficiency.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A particle collector, comprising:
   a cyclone unit that draws in a gas sample and creates a circular flow of said gas sample so that particles in said gas sample are separated from said gas sample by centrifugation force;
   a liquid delivery unit that delivers a collection liquid in a non-continuous fashion into said cyclone unit wherein said collection liquid traps the particles separated from said gas to form a particle-rich collection liquid, said liquid delivery unit comprises a collection liquid tank, a pump that maintains a positive pressure in said collection liquid tank, and a valve that controls delivery of said collection liquid to said cyclone unit, wherein said valve operates at a duty cycle of 5% to 50%; and
   a sample collection unit that harvests said particle-rich collection liquid from said cyclone unit.

2. The particle collector of claim 1, wherein said cyclone unit comprises: an aerosolization chamber; and a cyclone chamber having a gas sample inlet, a inner cyclone wall surrounding a gas sample passage, a gas sample out let, and a collection liquid outlet, where said gas sample enters said cyclone chamber through said gas sample inlet, passes through said gas sample passage and exits said cyclone chamber through said gas sample out let, and wherein said collection liquid is aerosolized in the aerosolization chamber, carried into said cyclone chamber by said gas sample and harvested as said particle-rich collection liquid at said collection liquid outlet.

3. The particle collector of claim 2, wherein said cyclone unit further comprises a thermoelectric cooler that provides cooling to said inner cyclone wall.

4. The particle collector of claim 2, wherein said cyclone unit further comprises an air blast atomizer that aerosolizes said collection liquid when it enters said aerosolization chamber.

5. The particle collector of claim 2, wherein said sample collection unit comprises: a particle-rich collection liquid reservoir that receives said article-rich collection liquid harvested at said collection liquid outlet; a flow meter; and a pump that maintains a pressure in said particle-rich collection liquid reservoir.

6. The particle collector of claim 5, wherein said flow meter is a non-contact flow meter.

7. The particle collector of claim 5, wherein said pump is a diaphragm pump.

8. The particle collector of claim 5, wherein said sample collection unit further comprises a pressure sensor that monitors the pressure inside said particle-rich collection liquid reservoir.

9. The particle collector of claim 1, wherein said valve is a solenoid valve.

10. The particle collector of claim 9, wherein said liquid delivery unit further comprises: a pressure sensor that monitors the pressure inside said collection liquid tank.

11. The particle collector of claim 1, wherein said valve operates on a duty cycle of 10%.

12. The particle collector of claim 1, wherein said pump is a diaphragm pump.

13. The particle collector of claim 1, further comprising a sample processing unit that processes the particle-rich collection fluid harvested by said sample collection unit for further analysis.

14. The particle collector of claim 13, further comprising a sample analysis unit for analyzing the particle-rich collection fluid processed by said sample processing unit for the presence of a target particle or molecule.

15. The particle collector of claim 1, further comprising a collection liquid recycling system that processes said particle-rich collection liquid harvested by said sample collection unit, and recycles the processed collection liquid back to said collection liquid delivery unit.

16. The particle collector of claim 1, further comprising a programmable logic controller (PLC) that is connected to said cyclone unit, said liquid delivery unit and said sample collection unit, wherein said PLC monitors and controls the operation of said cyclone unit, said liquid delivery unit and said sample collection unit.

17. The particle collector of claim 16, wherein said PLC comprises: a flash memory; a microcontroller; and an external port.

18. A method for collecting particles from a gas sample, comprising: introducing said gas sample into a cyclone chamber in a circular flow so that particles in said gas sample are separated from said gas sample by centrifugation force; introducing a collection liquid in a non-continuous fashion into said cyclone chamber, said collection liquid forms a thin liquid layer on an inner wall of said cyclone chamber and traps particles impacting on said inner wall to form a particle-rich collection liquid; and harvesting said particle-rich collection liquid from said cyclone chamber, wherein said collection liquid is introduced into said cyclone chamber from a collection liquid tank maintained under a positive pressure via a valve with a duty cycle of 5% to 50%.

19. The method of claim 18, further comprising cooling said inner wall of said cyclone during a collection period to reduce evaporation of said collection liquid.

20. The method of claim 18, wherein said collection liquid is introduced into said cyclone chamber from a collection liquid tank maintained under a positive pressure via a valve with a duty cycle of about 10%.

* * * * *